US009035106B2

(12) United States Patent
Garel et al.

(10) Patent No.: US 9,035,106 B2
(45) Date of Patent: May 19, 2015

(54) METHOD FOR THE HYDROXYLATION OF PHENOLS AND PHENOL ETHERS

(75) Inventors: Laurent Garel, Lyons (FR); Jean-Christophe Bigouraux, Dargoire (FR); Stéphanie Normand, Saint-Genis-Laval (FR); Pascal Pitiot, Lyons (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 13/984,966

(22) PCT Filed: Feb. 15, 2012

(86) PCT No.: PCT/EP2012/052584
§ 371 (c)(1),
(2), (4) Date: Sep. 9, 2013

(87) PCT Pub. No.: WO2012/110553
PCT Pub. Date: Aug. 23, 2012

(65) Prior Publication Data
US 2014/0221698 A1    Aug. 7, 2014

(30) Foreign Application Priority Data
Feb. 17, 2011   (FR) ...................................... 11 00485

(51) Int. Cl.
*C07C 37/60* (2006.01)
*C07C 37/08* (2006.01)

(52) U.S. Cl.
CPC ....................................... *C07C 37/60* (2013.01)

(58) Field of Classification Search
USPC ........................................................ 568/768
See application file for complete search history.

(56) References Cited

U.S. PATENT DOCUMENTS 3,849,502 A     11/1974  Bourdin et al.
4,453,024 A  *   6/1984  Jouannetaud et al. ........ 568/768
5,026,925 A      6/1991  Drauz et al.
5,245,086 A  *   9/1993  Costantini et al. ............ 568/629
5,434,317 A  *   7/1995  Costantini et al. ............ 568/768
5,714,641 A      2/1998  Costantini et al.
6,262,315 B1     7/2001  Inaba et al.
2004/0109798 A1  6/2004  Chopard et al.
2006/0159600 A1  7/2006  Chopard
2008/0140376 A1  6/2008  Elgue et al.
2012/0035397 A1  2/2012  Garel

FOREIGN PATENT DOCUMENTS

| EP | 0 230 625 A1 | 8/1987 |
| EP | 0 480 800 A1 | 4/1992 |
| FR | 2071464 A5 | 9/1971 |
| FR | 2823995 A1 | 10/2002 |
| FR | 2880967 A1 | 7/2006 |
| FR | 2 944 012 A1 | 10/2010 |
| JP | 11-310543 A | 11/1999 |
| JP | 11-343257 A | 12/1999 |
| JP | 2003-55287 A | 2/2003 |
| JP | 2005-200349 A | 7/2005 |
| WO | WO 02/37047 A1 | 5/2002 |
| WO | WO 02/058840 A1 | 8/2002 |
| WO | WO 02/085511 A1 | 10/2002 |
| WO | WO 2004045761 A1 | 6/2004 |
| WO | WO 2010115784 A1 | 10/2010 |
| WO | WO 2011117540 A1 | 9/2011 |

* cited by examiner

*Primary Examiner* — Brian J Davis
(74) *Attorney, Agent, or Firm* — Beatrice C. Ortego

(57) ABSTRACT

The present invention relates to a method for the hydroxylation of phenols and phenol ethers by means of hydrogen peroxide. The invention specifically relates to a method for the hydroxylation of phenol by means of the hydrogen peroxide. The method of the invention for the hydroxylation of a phenol or phenol ether by means of reacting said phenol or phenol ether with the hydrogen peroxide in the presence of an acid catalyst is characterized in that it includes mixing a phenol or phenol ether with a hydrogen peroxide solution in a mixing device under conditions enabling the conversion rate of the hydrogen peroxide to be minimized, and in that said reaction mixture is then placed in a piston flow reactor where the reaction leading to the production of the hydroxylated material takes place, the acid catalyst being fed into the mixing device and/or into the piston flow reactor.

24 Claims, 5 Drawing Sheets

METHOD FOR THE HYDROXYLATION OF PHENOLS AND PHENOL ETHERS

CROSS-REFERENCE TO RELATED APPLICATIONS

This application is a U.S. national stage entry under 35 U.S.C. §371 of International Application No. PCT/EP2012/052584 filed Feb. 15, 2012, which claims priority to French Application No. FR 1100485 filed on Feb. 17, 2011. The entire contents of these applications are explicitly incorporated herein by this reference.

The present invention relates to a process for hydroxylating phenols and phenol ethers with hydrogen peroxide.

The invention is more particularly directed toward a process for hydroxylating phenol with hydrogen peroxide.

In the description that follows of the present invention, the term "phenol substrate" is used without preference to denote a phenol or a phenol ether.

The reaction for the hydroxylation of phenol with hydrogen peroxide leads to the production of two isomers, namely 1,4-dihydroxybenzene or hydroquinone (HQ) and 1,2-dihydroxybenzene or pyrocatechol (PC).

In the present text, the term "diphenol" denotes hydroquinone and pyrocatechol.

Hydroquinone is a product used in many fields of application as a polymerization inhibitor, an antioxidant in elastomers, or as a synthetic intermediate. Another field of application is photography.

Pyrocatechol is also a product that is widely used, especially as a polymerization inhibitor or antioxidant in elastomers, olefins, polyolefins or polyurethane or as a tanning agent.

On account of its complexing properties, pyrocatechol is also used as a chelating agent especially in the electronics field and as a corrosion inhibitor.

It also serves as an intermediate in numerous syntheses, especially those of fragrances, cosmetics, medicaments and pesticides.

It follows that hydroquinone and pyrocatechol are mass-consumption products manufactured on a large scale.

Thus, given the size of the manufacturing volumes, it is important for their manufacturing process to be ideally optimized, in particular in terms of production efficiency, energy efficiency and yield.

Hydroquinone and pyrocatechol are conventionally produced by hydroxylation of phenol with hydrogen peroxide, in the presence of an acid catalyst, a strong protic acid or a solid catalyst with acidic properties, for instance TS-1.

One of the well-known routes for preparing said diphenols consists, according to FR 2 071 464, in performing the hydroxylation of phenol with hydrogen peroxide, in the presence of a strong protic acid, for instance sulfuric acid, chlorosulfuric acid or perchloric acid, or sulfonic acids, for instance methane sulfonic acid, trifluoromethanesulfonic acid, toluenesulfonic acid or phenolsulfonic acid. According to FR 2 944 012, this reaction is moreover improved by using a mixture of at least two strong acids, one being a strong protic acid and the other a superacid.

Hydrogen peroxide is used in the form of an aqueous solution.

Commercially sold hydrogen peroxide solution has a concentration of about 30%, which gives rise to drawbacks in the reaction since the presence of water slows down the reaction, and in the energy balance since this water must then be removed.

Recourse to more concentrated hydrogen peroxide solutions is desirable, but their use at the industrial scale is difficult since the risks of explosion are all the greater the higher the hydrogen peroxide concentration.

U.S. Pat. No. 5,026,925 teaches that the hydroxylation reaction of phenol in the presence of a strong acid, for instance perchloric acid or sulfuric acid, may be improved especially with regard to its yields. In this regard, said patent recommends changing the catalyst, in particular to use sulfur or selenium dioxide. U.S. Pat. No. 5,026,925 also indicates that it is possible to perform a reaction with an aqueous hydrogen peroxide solution. However, the illustrated aqueous solutions may comprise up to 85% of hydrogen peroxide, which is not a commercial grade.

Moreover, phenol is always used in large excess relative to the amount of hydrogen peroxide. Thus, the hydrogen peroxide/phenol mole ratio generally ranges between 0.01 and 0.3.

The presence of a large excess of phenol imposes, at the end of the reaction, the need to separate it from the reaction medium in order to recycle it.

This excess cost is proportionately more reduced the higher the degree of conversion of the phenol.

However, when the phenol hydroxylation reaction is performed in a conventionally used mixing device, such as a stirred reactor or a cascade of stirred reactors, the degree of conversion of the phenol is kept relatively low (less than 5%) to ensure good reaction performance. When the degree of conversion of the phenol is increased to reach 15-20%, the yields of diphenols obtained are divided by two. Specifically, the yield lowers since the level of byproducts increases especially via degradation of the diphenols, on account of the consecutive oxidation reactions.

It is thus very advantageous to increase the degree of conversion of the phenol by maintaining the selectivity and/or the yield of hydroquinone and pyrocatechol.

Thus, the object of the present invention is to provide an improved process for preparing hydroquinone and pyrocatechol in terms of material balance and energy efficiency.

A process has now been found, and it is this which constitutes the subject of the present invention, for the hydroxylation of a phenol or of a phenol ether by reacting said phenol or phenol ether with hydrogen peroxide, in the presence of a strong protic acid catalyst, characterized in that it comprises the mixing of a phenol or phenol ether with a hydrogen peroxide solution in a mixing device under conditions such that the degree of conversion of the hydrogen peroxide is minimized and said reaction mixture is then introduced into a piston-flow reactor in which takes place the reaction leading to the formation of the hydroxylated product; the acid catalyst being introduced into the mixing device and/or into the piston-flow reactor.

The process of the invention is performed in apparatus combining in sequence a mixing device in which the mixing of the reagents takes place and a piston-flow reactor in which the reaction is performed.

According to a first characteristic of the process of the invention, the mixing of the reagents takes place upstream of the piston-flow reactor in a device separate from said piston-flow reactor, which makes it possible to increase the process safety.

Thus, it is possible to make use of more concentrated aqueous hydrogen peroxide solutions whose concentration may range from 30% to 90% by weight and preferably from 30% to 70%. Specifically, the fact that the introduction of hydrogen peroxide is not performed directly into the piston-flow reactor provides safety in the event of an incident arising regarding the feed of the phenol substrate. Specifically, in the case where the process involves a concentrated hydrogen peroxide solution and when the introduction of the phenolic substrate ceases, there would be accumulation of hydrogen peroxide in the reaction medium and the conditions would then be met for them to become explosive.

According to a second characteristic of the process of the invention, the hydroxylation reaction of the phenolic substrate is performed essentially in the piston-flow reactor, which allows a gain in selectivity when compared with a process in which the hydroxylation reaction is performed in a cascade of stirred reactors. Specifically, good selectivity was obtained on account of a limitation of the subsequent reactions.

Another advantage of the process of the invention is that the degree of conversion of the phenolic substrate is increased, for example ranging from 5% to 15% and preferentially from 5% to 10%, such that the amount of residual phenolic substrate to be recycled is reduced, thus making it possible to lower the energy consumption.

Moreover, the fact that there is only one mixing device coupled to a piston-flow reactor presents the advantage of low bulk and also a saving in operating, energy and investment costs when compared with a cascade of perfectly stirred reactors, each equipped with means for introducing the reagents, for removing the products, and also devices for mixing the reagents and for controlling the process parameters.

Another advantage of the invention is that it leads to a gain in reaction yields.

Figure 5:
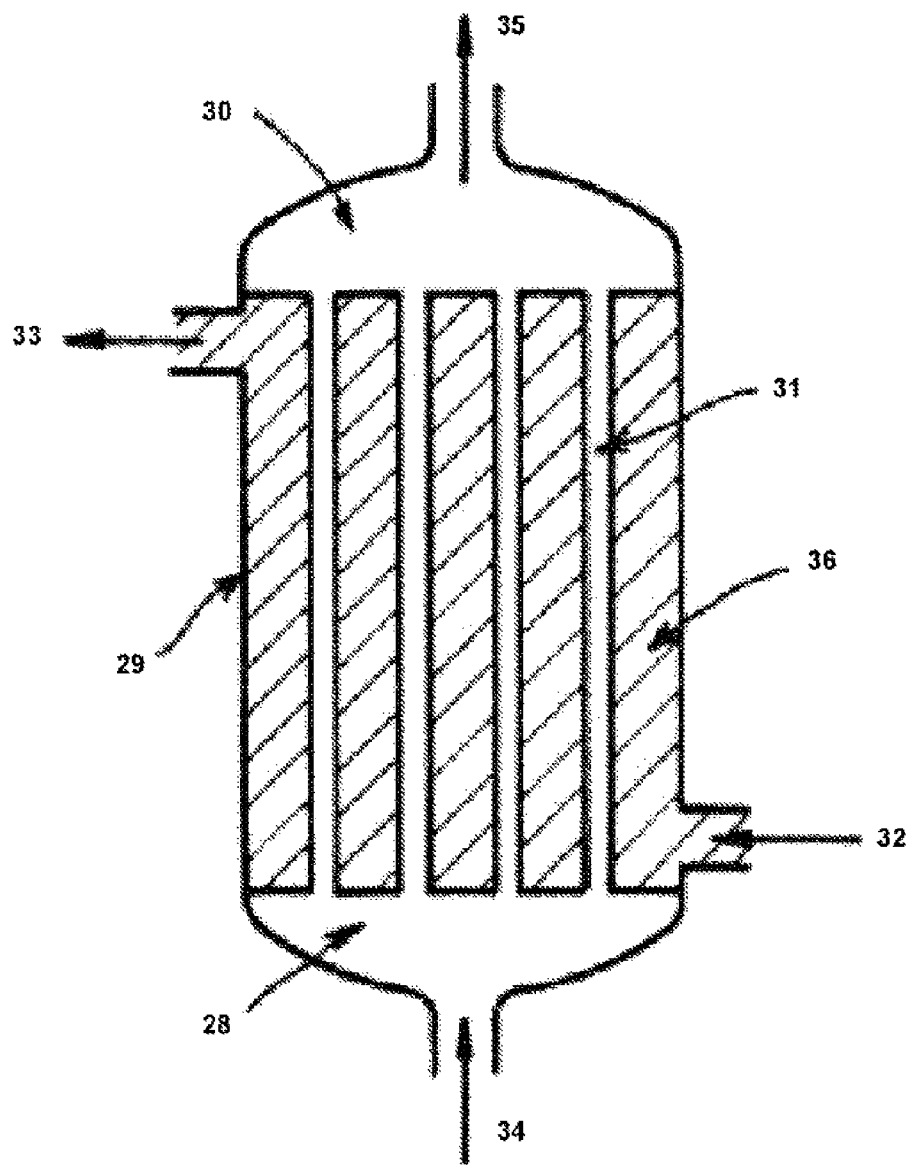

FIG. 5 schematically represents a multitubular reactor comprising tubes combined in a bundle that may be used as the piston-flow reactor in the reaction step according to the process of the invention.

Figure 1:
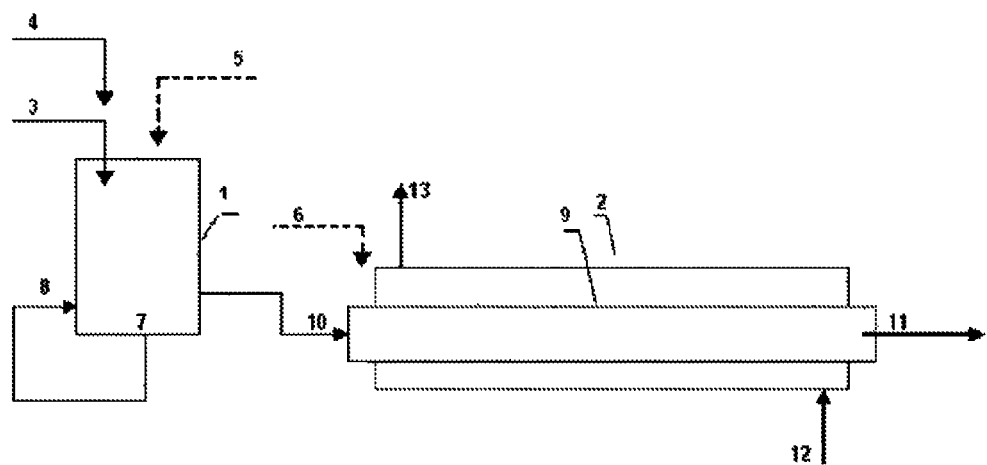
FIG. 1 is a schematic view of an apparatus suitable for performing the process of the invention in which a first step of mixing is performed in a mixing device and a second step relative to the hydroxylation reaction is performed in a piston-flow reactor.

A practical embodiment of the invention is illustrated in the attached drawing in the form of FIG. 1.

FIG. 1 is a schematic view of apparatus suitable for implementing the invention.

The apparatus used consists of two assemblies.

The first assembly comprises the reactor (1) equipped with means for introducing the reagents and for mixing.

The second assembly comprises a piston-flow reactor (2).

At the outlet of reactor (1), a reaction mixture is obtained, which is introduced into the piston-flow reactor (2).

The process of the invention is performed in the liquid phase, but the invention does not exclude a gaseous phase.

At the outlet of reactor (2), the hydroxylated phenolic substrate is obtained.

According to a first characteristic of the process of the invention, the mixing of the phenolic substrate and of the hydrogen peroxide solution is performed in a mixing device (1): the acid catalyst may be introduced into this reactor and/or into the piston-flow reactor.

The mixing operation is performed such that the reaction does not start or starts very little during this step.

Thus, it is desirable for the degree of conversion of the hydrogen peroxide to be less than 25 mol %, preferably between 0.5 mol % and 25 mol % and even more preferentially between 0.5 mol % and 15 mol %.

To do this, the temperature of this mixing operation is advantageously chosen to be not more than 70° C. and preferably between 45° C. and 70° C.

According to another characteristic of the process of the invention, the reaction is performed essentially in a piston-flow reactor (2).

To this end, the temperature in said reactor is higher than that in the mixing device. It is chosen to be higher than 70° C., preferably between 75° C. and 200° C. and more preferentially between 75° C. and 150° C.

According to preferred embodiments, the reactor is a tubular reactor or a column reactor.

In the description that follows of the present invention, the term "tubular reactor" means a reactor in the form of a tube, and the term "column reactor" means a vertical reactor of circular cross section.

The term "piston flow" defines a unidirectional flow in which, in a plane perpendicular to the flow, all the fluid streams travel with a uniform speed. In such a flow, the radial mixing is perfect, whereas there is no axial mixing. In practice, these conditions are considered as being met when the flow is turbulent.

It is estimated that a flow is turbulent when the Reynolds number is greater than or equal to 5000 and preferentially when it is greater than 10 000. When the flow is not turbulent, the radial mixing is not perfect and there may be axial back-mixing. In this case, for a Reynolds number of less than about 5000 and more particularly less than 2000, the tubular reactor or the column reactor is packed with baffles and/or is structured.

It is recalled that the definition of the Reynolds number is:

$$Re = \frac{\rho \cdot v \cdot d}{\mu}$$

in which:

$\rho$ is the mass per unit volume of the fluid in kg/m$^3$;

v is the flow rate in m/s;

d is the diameter of the reactor in m;

$\mu$ is the dynamic viscosity in Pa·s

Generally, Re is between 1 and 1 000 000.

Figure 2:
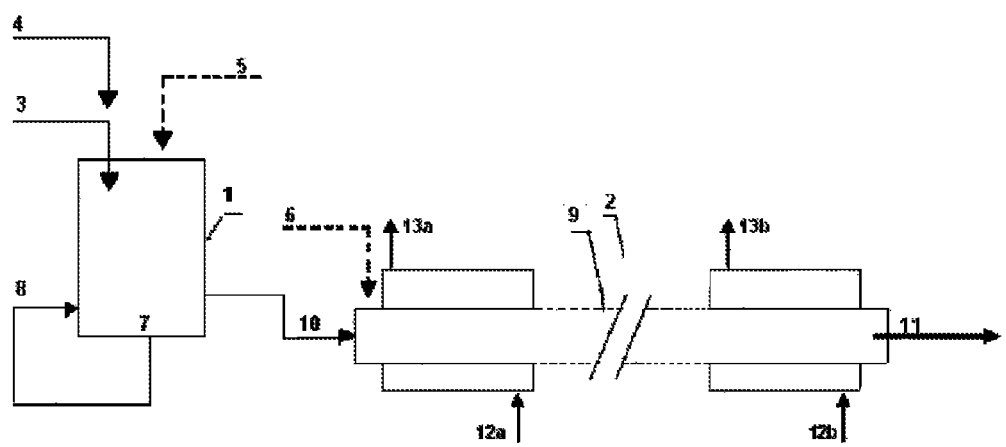
FIG. 2 is a schematic view of apparatus suitable for performing a variant of the process of the invention in which the piston-flow reactor is configured such that the reaction temperature is staged.

FIG. 2 is a schematic view of apparatus suitable for performing a variant of the process of the invention in which the piston-flow reactor is configured such that the reaction temperature is staged.

Figure 3:
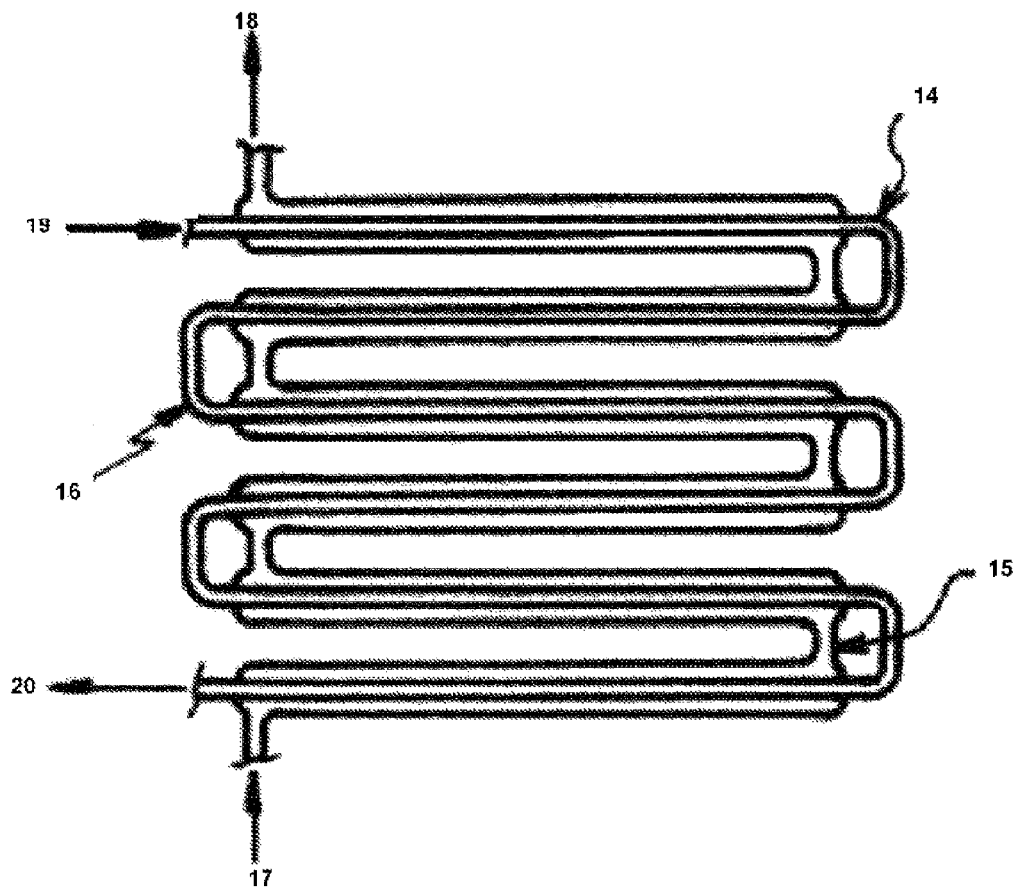
FIG. 3 is a schematic representation of a tubular reactor formed from concentric tubes that may be used as the piston-flow reactor in the reaction step according to the process of the invention.
Figure 4:
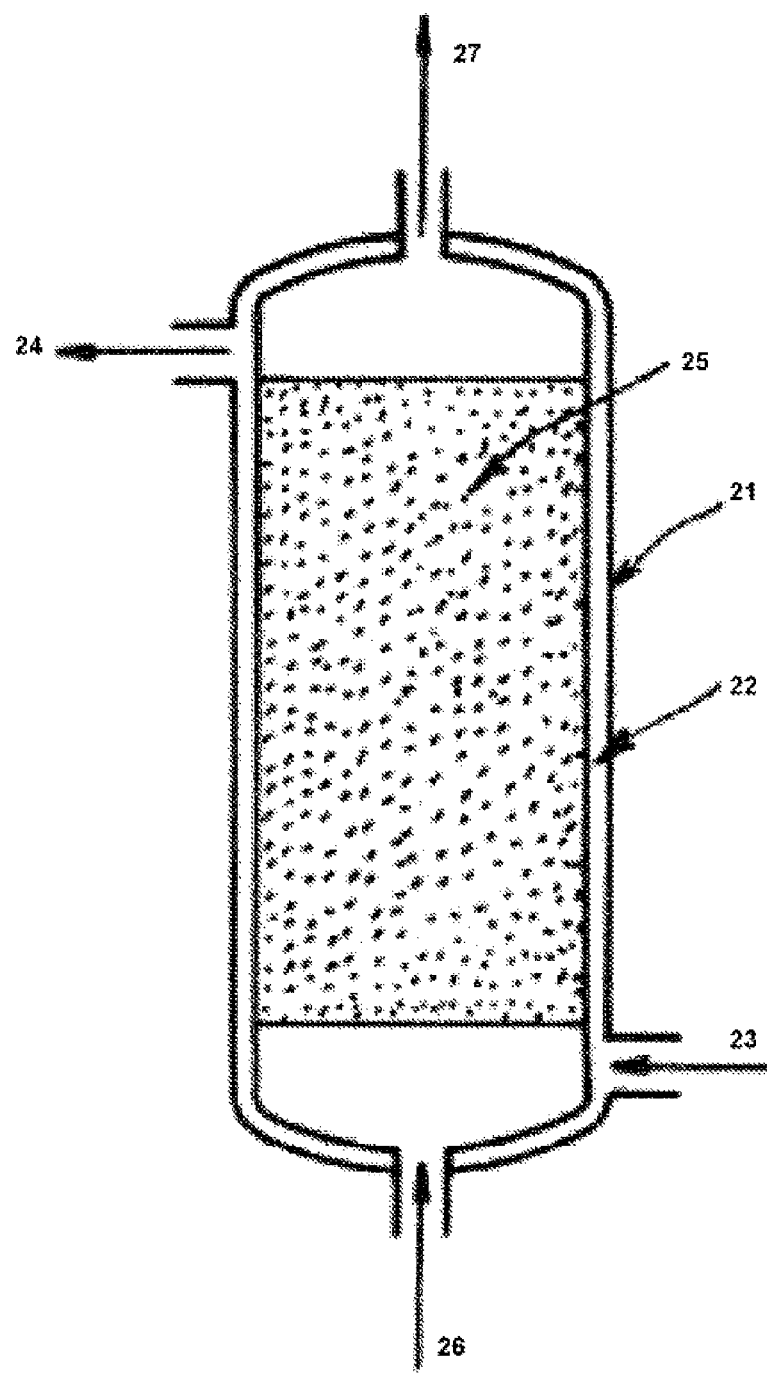
FIG. 4 is a schematic representation of a reactor in column form that may be used as the piston-flow reactor in the reaction step according to the process of the invention.

FIGS. 3 to 5 illustrate types of piston-flow reactors that may be used in the process of the invention.

FIG. 3 is a schematic representation of a tubular reactor formed from concentric tubes.

FIG. 4 is a schematic representation of a reactor in column form.

FIG. 5 schematically represents a multitubular reactor comprising tubes combined in a bundle.

A more detailed account of the means of the invention is given hereinbelow in the present description.

The described process proposes to perform a hydroxylation reaction of a phenol or of a phenol ether.

The aromatic nucleus bears at least one hydroxyl group or an ether function.

The process of the invention applies both to phenols and to phenol ethers, which are also referred to in the present text as "phenolic substrate".

The process of the invention is suitable for the hydroxylation of phenol or of a phenol ether, but also for substituted phenols or phenol ethers.

The term "substituted phenol or phenol ether" means a phenol or a phenol ether in which one of the hydrogen atoms of the aromatic ring is replaced with one or more substituents.

Generally, the term "several substituents" defines less than four substituents per aromatic nucleus.

Any substituent may be present, provided that it does not interfere in the reaction of the invention.

Thus, the process of the invention is suitable for being applied to phenolic substrates of general formula (I):

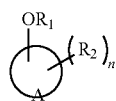

(I)

in which:
A symbolizes a benzene or naphthalene ring,
$R_1$ represents a hydrogen atom or an alkyl, cycloalkyl, aryl or aralkyl group,
$R_2$ represents a hydrogen atom or one or more identical or different substituents,
n, number of substituents per aromatic ring, is a number less than or equal to 4.

In formula (I) the group $OR_1$ is an ether group when $R_1$ is other than a hydrogen atom.

The number of substituents per aromatic ring is variable and generally less than or equal to 4, and preferably equal to 0, 1, 2 or 3.

Preferred examples of substituents are given for formula (Ia).

Thus, the process of the invention is suitable for phenolic substrates corresponding to formula (I) in which A represents a benzene ring and which are represented more particularly by the general formula (Ia):

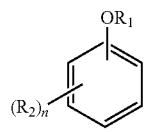

(Ia)

in said formula:
n is a number from 0 to 4 and preferably equal to 0, 1, or 2,
$R_1$ represents a hydrogen atom or an alkyl, cycloalkyl, aryl or aralkyl group,
$R_2$, which may be identical or different, represent an alkyl group, an alkoxy group, a hydroxyl group, a halogen atom or a haloalkyl or perhaloalkyl group.

The process of the invention preferentially applies to substrates corresponding to formula (Ia) in which n is equal to 0 or 1; $R_1$ represents a hydrogen atom or an alkyl group containing from 1 to 4 carbon atoms; $R_2$ represents a hydrogen atom or an alkyl or alkoxy group containing from 1 to 4 carbon atoms.

In formulae (I) and (Ia), the term "alkyl" means a linear or branched $C_1$-$C_{15}$, preferably $C_1$-$C_{10}$ and even more preferentially $C_1$-$C_4$ hydrocarbon-based chain. Examples of preferred alkyl groups are especially methyl, ethyl, propyl, isopropyl, butyl, isobutyl and t-butyl.

The term "alkoxy" means a group alkyl-O— in which the term "alkyl" has the meaning given above. Preferred examples of alkoxy groups are methoxy or ethoxy groups.

The term "cycloalkyl" means a $C_3$-$C_8$ monocyclic cyclic hydrocarbon-based group, preferably a cyclopentyl or cyclohexyl group.

The term "aryl" means a monocyclic or polycyclic aromatic, preferably $C_6$-$C_{20}$ monocyclic or bicyclic group, preferably phenyl or naphthyl. When the group is polycyclic, i.e. when it comprises more than one cyclic nucleus, the cyclic nuclei may be fused in pairs or attached in pairs via σ bonds. Examples of ($C_6$-$C_{18}$)aryl groups are especially phenyl and naphthyl.

The term "aralkyl" means a linear or branched hydrocarbon-based group bearing a $C_7$-$C_{12}$ monocyclic aromatic ring, preferably benzyl: the aliphatic chain comprising 1 or 2 carbon atoms.

The term "haloalkyl group" means an alkyl group as defined previously in which one or more hydrogen atoms are replaced with a halogen atom, preferably a fluorine atom.

The term "perhaloalkyl group" means an alkyl group comprising from 1 to 10 carbon atoms and from 3 to 21 halogen atoms, preferably fluorine, and more particularly the trifluoromethyl group.

The term "halogen atom" defines fluorine, chlorine and bromine.

As illustrations of phenolic substrates of formula (I) that may be used in the process of the invention, mention may be made more particularly of:
those corresponding to formula (I) in which n is equal to 0, such as phenol or anisole,
those corresponding to formula (I) in which n is equal to 1, such as o-cresol, m-cresol, p-cresol, 2-ethylphenol, 3-ethylphenol, 2-propylphenol, 2-sec-butylphenol, 2-tert-butylphenol, 3-tert-butylphenol, 4-tert-butylphenol, 2-methoxyphenol, 3-methoxyphenol, 4-methoxyphenol, 2-ethoxyphenol, methyl salicylate, 2-chlorophenol, 3-chlorophenol or 4-chlorophenol,
those corresponding to formula (I) in which n is equal to 2, such as 2,3-dimethylphenol, 2,5-dimethylphenol, 2,6-dimethylphenol, 3,5-dimethyphenol, 2,3-dichlorophenol, 2,5-dichlorophenol, 2,6-dichlorophenol, 3,5-dichlorophenol, 2,6-di-tert-butylphenol or 3,5-di-tert-butylphenol,
those corresponding to formula (I) in which n is equal to 3, such as 2,3,5-trimethylphenol, 2,3,6-trimethylphenol, 2,3,5-trichlorophenol or 2,3,6-trichlorophenol,
those corresponding to formula (I) in which A represents a naphthalene ring, such as 1-hydroxynaphthalene.

Among the abovementioned phenolic substrates, use is preferentially made of phenol, o-cresol, m-cresol, p-cresol, anisole, phenetole, 2-methoxyphenol (guaicol) or 2-ethoxyphenol (guetol).

The present process is most particularly suitable for preparing hydroquinone and pyrocatechol from phenol.

An acid catalyst which is a strong acid is used in the process of the invention. In the present invention, the term "strong acid" denotes an acid with a pKa in water of less than −0.1 and preferably less than −1.0.

The pKa is defined as being the ionic dissociation constant of the acid/base couple, when water is used as solvent.

Among the acids corresponding to this definition, it is preferable to use those that are stable with respect to oxidation with hydrogen peroxide.

Mention may be made more particularly of halogenated or non-halogenated oxy acids such as sulfuric acid, phosphoric acid, pyrosulfuric acid, perchloric acid; aliphatic or aromatic sulfonic acids, for instance methanesulfonic acid, ethanesulfonic acid, benzenesulfonic acid, toluenesulfonic acids, naphthalenesulfonic acids, benzenedisulfonic acids, naphthalenedisulfonic acids; halosulfonic acids such as fluorosulfonic acid, chlorosulfonic acid, bis-trifluoromethanesulfonimide or trifluoromethanesulfonic acid.

Among the abovementioned acids, sulfuric acid, perchloric acid, methanesulfonic acid, trifluoromethanesulfonic acid, toluenesulfonic acid, phenol sulfonic acid and bis-trifluoromethanesulfonimide are preferably used.

According to one variant of the process of the invention, it is possible to use as strong protic acid a hydroxyaromatic sulfonic acid as described in WO 2009/150 125.

As preferred examples of hydroxyaromatic sulfonic acids preferentially used in the process of the invention, mention may be made of the acids corresponding to the following formula:

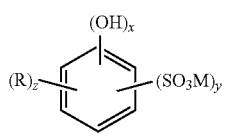

(Ia)

in said formula:
 x is equal to 1, 2 or 3, preferably 1 or 2,
 y is equal to 1 or 2,
 z is a number from 0 to 4 and preferably equal to 0, 1, or 2,
 M represents a hydrogen, sodium or potassium atom,
 R represents an alkyl or alkoxy group containing from 1 to 4 carbon atoms or a carboxylic group.

Among the acids that are suitable for use in the process of the invention, mention may be made more particularly of hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids and hydroxynaphthalenedisulfonic acids, and mixtures thereof.

Among the hydroxybenzenesulfonic acids, use will preferably be made of 4-hydroxybenzenesulfonic acid, 2-hydroxybenzenesulfonic acid or 5-sulfosalicylic acid, or a mixture thereof.

As preferred examples of dihydroxybenzenesulfonic acids used, mention may be made of sulfonic acids resulting from the sulfonation of hydroquinone (1,4-dihydroxybenzene), of pyrocatechol (1,2-dihydroxybenzene) and of resorcinol (1,3-dihydroxybenzene).

The preferred dihydroxybenzenedisulfonic acids are 5,6-dihydroxy-1,3-benzenedisulfonic acid, 4,6-dihydroxy-1,3-benzenedisulfonic acid and 2,5-dihydroxy-1,4-benzenedisulfonic acid.

The sulfonic hydroxyaromatic acids are available in solid or liquid form or as an aqueous solution whose concentration may range between 5% and 95% by weight and preferably between 50% and 70% by weight.

According to another variant of the process of the invention, it is possible to use a mixture of at least two strong protic acids, as described in WO 2010/115 784.

The mixture comprises two acids (A) and (B) having specific respective pKa values: the acid (B) being much stronger than the acid (A).

Said mixture comprises:
 a strong acid (A) with a $pK_a$ (S) greater than or equal to that of sulfuric acid and a $\Delta pK_a$ (S) relative to sulfuric acid of less than or equal to 4 and greater than or equal to 0,
 and another acid (B) chosen from superacids.

The acid (A) has a $pK_a$ (S) greater than or equal to that of sulfuric acid: (S) representing the organic solvent, which is nitrobenzene.

The acid (B) is a superacid, which is defined as having a $pK_a$ (S) less than that of sulfuric acid.

The $pK_a$ (S) is defined as being the ionic dissociation constant of the acid/base couple in a solvent (S).

The $pK_a$ of the acids is defined by reference to a potentiometry measurement performed in a solvent which is nitrobenzene (S), and the measuring protocol of which is described before the examples of WO 2010/115 784.

The acids used in said mixture are defined by a $pK_a$ difference, $\Delta pK_a$, which corresponds for the same solvent to the difference between the $pK_a$ of the chosen acid and the $pK_a$ of sulfuric acid.

The acid (A) used has a $\Delta pK_a$ (S) relative to sulfuric acid of less than or equal to 4 and greater than or equal to 0.

Even more preferentially, the acid (A) has a $\Delta pK_a$ (S) relative to sulfuric acid of less than or equal to 3 and greater than or equal to 0.

Examples of acids (A) that may especially be mentioned include sulfuric acid, aliphatic or aromatic sulfonic acids, for instance methanesulfonic acid, ethanesulfonic acid, benzenesulfonic acid, toluenesulfonic acids and naphthalenesulfonic acids.

Another class of acids (A) is that of hydroxybenzenesulfonic acids, sulfonated hydroxybenzoic acids; hydroxybenzenedisulfonic acids, dihydroxybenzenedisulfonic acids, hydroxytoluenesulfonic acids, hydroxynaphthalenesulfonic acids and hydroxynaphthalenedisulfonic acids, and mixtures thereof.

Among the abovementioned acids, the preferred acids are 4-hydroxybenzenesulfonic acid, 2-hydroxybenzene sulfonic acid, 5-sulfosalicylic acid, sulfonic acids resulting from the sulfonation of hydroquinone (1,4-dihydroxybenzene), of pyrocatechol (1,2-dihydroxybenzene) and of resorcinol (1,3-dihydroxybenzene); 5,6-dihydroxy-1,3-benzenedisulfonic acid, 4,6-dihydroxy-1,3-benzenedisulfonic acid and 2,5-dihydroxy-1,4-benzenedisulfonic acid.

Other examples of acids that may especially be mentioned include perhaloacetic acids such as trichloroacetic acid and trifluoroacetic acid.

As regards the second component (B) of the mixture of acids, it is a superacid, i.e. an acid with a $pK_a$ (S) lower than that of sulfuric acid and which thus has a negative $\Delta pK_a$.

The lower limit is not critical, but, generally, the $\Delta pK_a$ in nitrobenzene is less than or equal to −12.

The superacids preferentially chosen have a $\Delta pK_a$ of less than or equal to −0.1 and preferably greater than or equal to −8.

Examples of superacids (B) that may be mentioned include perchloric acid, halosulfonic acids such as fluorosulfonic acid or chlorosulfonic acid; perhaloalkanesulfonic acids, preferably trifluoromethanesulfonic acid.

Superacids (B) that may also be mentioned include, inter alia, trifluoromethanesulfonic acid; bis-trifluoromethanesulfonimide.

As preferentially chosen pairs of acids (A) and (B), mention may be made of perchloric acid and sulfuric acid; perchloric acid and 4-hydroxybenzenesulfonic acid; trifluoromethanesulfonic acid and 4-hydroxybenzenesulfonic acid; bis-trifluoromethanesulfonimide and 4-hydroxybenzenesulfonic acid.

The proportion in the mixture of the various acids may vary widely.

Thus, use may be made of mixtures comprising:
from 60 mol % to 95 mol % and preferably from 80 mol % to 95 mol % of an acid (A),
from 5 mol % to 40 mol % and preferably from 5 mol % to 20 mol % of an acid (B).

Each percentage of acid expresses the ratio (expressed as a percentage) between the number of moles of the acid under consideration and the number of moles of the sum of the two acids (A) and (B).

The acids used in the mixture are commercially available in solid or liquid form or as an aqueous solution whose concentration may range between 5% and 95% by weight and preferably between 50% and 70% by weight.

The strong protic acid or the mixture of acids is used in the process of the invention in an amount, expressed by the ratio of the number of equivalents of protons to the number of moles of phenolic substrate, which advantageously ranges between 0.002% and 0.15%. Thus, said mole ratio is preferentially chosen between 0.01% and 0.07%.

According to another variant of the process of the invention, the hydroxylation of the phenolic substrate is performed in the presence of a cocatalyst, which is a ketone compound, and more particularly those corresponding to formula (II):

$$R_a—CO—X—R_b \quad (II)$$

in which formula (II):
$R_a$ and $R_b$, which may be identical or different, represent hydrocarbon-based groups containing from 1 to 30 carbon atoms or together form a divalent group, optionally substituted with one or more halogen atoms or functional groups that are stable under the reaction conditions,
X represents a valency bond, a —CO— group, a —CHOH group or a group —(R)$_n$—: R representing an alkylene group preferably containing from 1 to 4 carbon atoms and n is an integer chosen between 1 and 16.

In formula (II), $R_a$ and $R_b$ more particularly represent:
linear or branched alkyl groups,
linear or branched alkenyl groups,
cycloalkyl or cycloalkenyl groups comprising from 4 to 6 carbon atoms,
monocyclic or polycyclic aryl groups; in the latter case, the rings together forming an ortho- or ortho- and peri-fused system or being linked together via a valency bond,
arylalkyl or arylalkenyl groups,
$R_a$ and $R_b$ may together form an alkylene or alkenylene group comprising from 3 to 5 carbon atoms, optionally substituted with an alkyl group with low carbon condensation or with a cycloalkyl or cycloalkenyl group containing 4 to 6 carbon atoms; 2 to 4 of the carbon atoms of the alkylene or alkenylene groups possibly forming part of one or two benzene rings optionally substituted with 1 to 4 hydroxyl and/or alkyl and/or alkoxy groups with low carbon condensation.

In the description that follows of the invention, the term "alkyl group of low carbon condensation" means a linear or branched alkyl group generally containing from 1 to 4 carbon atoms.

The abovementioned hydrocarbon-based groups may be substituted with one or more, preferably 1 to 4, alkyl groups of low carbon condensation or functional groups such as hydroxyl groups, alkoxy groups of low carbon condensation, hydroxycarbonyl or alkyloxycarbonyl groups comprising from 1 to 4 carbon atoms in the alkyl group, a nitrile, sulfonic or nitro group, or with one or more halogen atoms, and especially chlorine and bromine.

Preferably, $R_a$ and $R_b$ more particularly represent:
linear or branched alkyl groups containing from 1 to 10 carbon atoms,
linear or branched alkenyl groups containing from 2 to 10 carbon atoms,
cycloalkyl or cycloalkenyl groups comprising from 4 to 6 carbon atoms,
phenyl groups optionally substituted with 1 to 4 alkyl and/or hydroxyl and/or alkoxy groups,
phenylalkyl or phenyl alkenyl groups comprising 1 (or 2) to 10 carbon atoms in the aliphatic part, and even more particularly from 1 (or 2) to 5 carbon atoms in the aliphatic part,
$R_a$ and $R_b$ may together form an alkylene or alkenylene group comprising from 3 to 5 carbon atoms, optionally substituted with 1 to 4 alkyl groups with low carbon condensation.

Thus, use is made most particularly of ketone compounds of dialkyl ketone type corresponding to formula (II) in which $R_a$ and $R_b$ represent a linear or branched alkyl group containing from 1 to 8 carbon atoms.

Among all the ketone compounds corresponding to formula (II), the ones that are preferentially chosen are those corresponding to formula (II) in which $R_a$ and $R_b$ represent an optionally substituted phenyl group.

The said ketone compounds may be represented by formula (IIa) below:

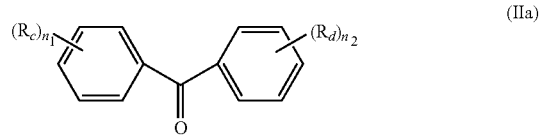

in said formula (IIa):
$R_c$ and $R_d$, which may be identical or different, represent a hydrogen atom or a substituent, preferably an electron-donating group,
$n_1$ and $n_2$, which may be identical or different, represent a number equal to 0, 1, 2 or 3,
optionally, the two carbon atoms located α to the two carbon atoms bearing the —CO group may be linked together via a valency bond or via a —CH$_2$— group, thus forming a ketone ring, which may be saturated, but also unsaturated.

The substituent is chosen such that it does not react under the acidity conditions of the invention. It is preferentially an electron-donating group.

The term "electron-donating group" means a group as defined by H. C. Brown in the book by Jerry March—Advanced Organic Chemistry, chapter 9, pages 243 and 244 (1985).

Examples of substituents that are suitable for use in the invention are the following:
linear or branched alkyl groups containing from 1 to 4 carbon atoms,
a phenyl group,
alkoxy groups comprising a linear or branched alkyl chain containing from 1 to 4 carbon atoms or a phenoxy group,
a hydroxyl group,
a fluorine atom.

As examples of ketone compounds that are particularly suitable for use in the invention, mention may be made most particularly of the ketone compounds corresponding to the general formula (IIa) in which $R_c$ and $R_d$, which may be identical or different, represent a hydrogen atom or a substituent as mentioned previously, preferably in position 4,4', and $n_1$ and $n_2$, which may be identical or different, are equal to 0 or 1.

Use is preferentially made of the ketone compounds corresponding to formula (IIa) in which $R_c$ and $R_d$, which may be identical or different, represent a hydrogen atom; a methyl, ethyl, tert-butyl or phenyl group; a methoxy or ethoxy group; a hydroxyl group, preferably in position 3,3' or 4,4'.

As specific examples of ketones that may be used in the process of the invention, mention may be made more particularly of:
benzophenone
2-methylbenzophenone
2,4-dimethylbenzophenone
4,4'-dimethylbenzophenone
2,2'-dimethylbenzophenone
4,4'-dimethoxybenzophenone
4-hydroxybenzophenone
4,4'-dihydroxybenzophenone
4-benzoylbiphenyl.

The amount of ketone compound used, expressed by the ratio between the number of moles of ketone compound and the number of moles of phenolic compound, may range between 0.01% and 20% and preferably between 0.1% and 2%.

In accordance with the process of the invention, a phenol or a phenol ether is reacted with hydrogen peroxide, in the presence of a strong protic acid and optionally of a ketone.

The hydrogen peroxide used according to the invention may be in the form of an aqueous solution or an organic solution.

Since the aqueous solutions are more readily commercially available, they are preferably used.

The concentration of the aqueous hydrogen peroxide solution, although not critical per se, is chosen so as to introduce as little water as possible into the reaction medium. An aqueous hydrogen peroxide solution with an $H_2O_2$ concentration of at least 20% by weight and preferably between 20% and 90% by weight is generally used.

An aqueous hydrogen peroxide solution with an $H_2O_2$ weight concentration ranging from 30% to 90% and preferably from 30% to 70% is advantageously chosen.

The amount of hydrogen peroxide may range up to 0.5 mol of $H_2O_2$ per 1 mol of substrate of formula (I).

However, in order to obtain an industrially acceptable yield, it is preferable to use a hydrogen peroxide/phenolic substrate mole ratio of from 0.01 to 0.3 and preferably from 0.03 to 0.10.

Since the amount of water has an influence on the reaction rate, it is preferable to minimize its presence: water may be introduced into the reaction medium especially by the reagents used.

An initial water content of the medium of less than 20% by weight and preferably less than 10% by weight should preferentially be chosen.

The indicated weight contents of water are expressed relative to the mixture of substrate of formula (I)/hydrogen peroxide/water.

This initial water corresponds to the water introduced with the reagents and especially with the hydrogen peroxide.

One variant of the process of the invention consists in adding an agent for complexing the metal ions present in the medium since they are harmful to the correct procedure of the process of the invention, especially in the case of phenols in which the yields of hydroxylation products are low. Consequently, it is preferable to inhibit the action of the metal ions.

The metal ions that are harmful to the procedure of the hydroxylation are transition metal ions and more particularly iron, nickel, copper, chromium, cobalt, manganese and vanadium ions.

The metal ions are introduced by the reagents and especially the starting substrates and the apparatus used. To inhibit the action of these metal ions, it suffices to perform the reaction in the presence of one or more complexing agents that are stable with respect to hydrogen peroxide and which give complexes that cannot be decomposed with the strong acids present and in which the metal can no longer exert any chemical activity.

As nonlimiting examples of complexing agents, use may be made especially of the various phosphoric acids, for instance orthophosphoric acid, meta-phosphoric acid, pyrophosphoric acid, polyphosphoric acids, phosphonic acids such as (1-hydroxyethylidene)diphosphonic acid, phosphonic acid, ethylphosphonic acid or phenylphosphonic acid.

Use may also be made of esters of the abovementioned acids, and mention may be made more particularly of monoalkyl or dialkyl, monocycloalkyl or dicycloalkyl, or monoalkylaryl or dialkylaryl orthophosphates, for example ethyl or diethyl phosphate, hexyl phosphate, cyclohexyl phosphate or benzyl phosphate.

The amount of complexing agent depends on the metal ion content of the reaction medium.

There is obviously no upper limit, and the amount of complexing agents present may be largely in excess relative to that necessary to complex the metal ions. Generally, an amount representing from 0.01% to 2% and preferably from 0.01% to 0.3% by weight of the reaction medium is suitable for use.

The hydroxylation process is generally performed without any solvent other than that originating from the reagents, such as the solvent for the hydrogen peroxide.

The reaction may, however, also be performed in an organic solvent.

The solvents used must be stable in the presence of hydrogen peroxide.

Mention may be made of nonpolar solvents such as chlorinated aliphatic hydrocarbons, for example dichloromethane, tetrachloromethane and dichloroethane.

Use may also be made of more polar solvents, especially ethers, for example sulfolane or 1,2-dimethoxyethane, but also acetonitrile, 2-methylglutaronitrile, adiponitrile and dimethyl carbonate.

In order to facilitate the understanding of the process of the invention, reference is made to FIG. 1 which schematically shows the steps of the process of the invention, without, however, limiting the scope of the invention thereto.

In accordance with the process of the invention, a first step of mixing of the reagents is performed, in the mixing device (1).

A first class of mixing devices concerns mechanically stirred reactors. The reactor is generally of vertical cylindrical form with a flat or elliptical base.

This reactor is equipped with means for introducing the reagents, heating means, a stirring system, and, at the bottom or top, a system for withdrawing the reaction mixture. The reactor is also equipped with a device for measuring the temperature and pressure.

The mixing is performed in a reactor which has good performance qualities in terms of material transfer and heat transfer.

The stirring system, not shown in FIG. 1, may be a rotary stirrer.

Examples of stirrers that may be mentioned include, inter alia, a turbine with straight or inclined paddles or a marine impeller or any mobile "hydrofoil".

A second class of mixing devices concerns external loops. The mixing of the reaction medium then takes place by circulation in a loop of a fraction or all of the contents of the reactor, mechanically stirred or not, by means of a pump on an external loop.

A third class of mixing devices combines mixers without a rotating part, known as dynamic mixers, on the one hand, and static mixers, on the other hand.

In the family of dynamic mixers, mention may be made of tangential jet mixers, impact jet mixers, T or Y mixers, multi-lamination mixers, or ejectors.

For the "static" mixers, various interiors may be listed, such as the static mixers (Sulzer SMX, Kenics, etc.), a bulk bed of beads or particles, metallic or ceramic foams, etc.

All these mixers force the streams of fluids fed in to exchange matter with each other by dividing into substreams or by creating small-scale structures. These structures increase the contact surface between the flows of reagents.

The exchange surface for the heat transfer may be increased by means of coils or plates present inside the reactor or via a heat-exchange fluid circulating in a jacket.

Heat-exchange fluids that may be mentioned include, inter alia, water, steam or a suitable organic solvent, for instance an aromatic ether such as diphenyl ether and/or benzyl ether, a silicone oil, a paraffin and/or naphthenic oil, petroleum distillation residues, etc.

It has been discovered, surprisingly, that by increasing the reaction temperature in the piston-flow reactor, the reaction time is decreased and thus the volume of the reactor at a given flow rate is decreased, while at the same time conserving the performance of the chemical reaction, i.e. while conserving a high conversion of the hydrogen peroxide and the phenol and high selectivity toward hydroxylated products starting with phenol or phenol ether. This decrease in reaction time makes it possible to use commercial piston-flow reactors of the heat exchanger type.

According to a variant of the invention, the piston-flow reactor has an HS/V ratio of greater than or equal to 20 kW/($m^3 \cdot K$) and preferably greater than or equal to 100 kW/($m^3 \cdot K$), more preferably between 200 and 20 000 kW/($m^3 \cdot K$), in which H represents the global heat transfer coefficient in W/($m^2 \cdot K$), S represents the heat exchange surface area ($m^2$), and V represents the reaction volume in $m^3$. A piston-flow reactor with an HS/V ratio of between 200 and 4000 kW/($m^3 \cdot K$) is preferably used.

Typically, a jacketed tubular reactor, a calendar-type heat exchange tubular reactor or a plate-type heat exchange reactor may be used. As plate-type heat exchange reactors, mention may be made of the technology from Alfa-Laval as described in patent applications FR 2 823 995, US 2004/0 109 798, FR 2 880 967, WO 2002/085 511, US 2006/0 159 600 and EP 1 562 699, that of Chart and BHR Group with the Marbond TM Hex Reactor, described especially in WO 02/37047 and WO 02/058 840, and that of Heatric IP PCR. Mention may also be made of international patent application WO 2011/117 540 from Rhodia, which especially describes piston-flow heat exchange reactors equipped with one or more tubular reactors arranged in a chamber comprising a heat-exchange fluid. Heat-exchange fluids that may be mentioned include, inter alia, water, steam or a suitable organic solvent, for instance an aromatic ether such as diphenyl ether or and/or benzyl ether, a silicone oil, a paraffin and/or naphthenic oil, petroleum distillation residues, etc.

From a practical point of view, the phenol (3) and a hydrogen peroxide solution (4) are introduced into the mixing device (1).

In the case of the presence of a complexing agent and/or of a solvent, they may be introduced, for example, into the phenol.

The catalyst is introduced at (5) or optionally at the top (6) of the piston-flow reactor.

The catalyst may also be introduced fractionally at (5) and (6).

The various reagents are introduced gradually, preferably continuously, their rate of introduction being regulated by means of a pump.

The mixture of reagents is obtained as mentioned previously and FIG. 1 illustrates the production of the mixture by establishing a recirculation loop as illustrated in FIG. 1.

Part of the reaction mixture is withdrawn at the bottom of the reactor at (7) and is then introduced into the reactor at (8): the forced circulation of the mixture being ensured by a pump, not shown in scheme.

As mentioned previously, the mixing is performed under conditions such that the reaction is minimized.

Thus, the temperature is chosen such that it is less than or equal to 70° C. and preferably between 45° C. and 70° C.

The reaction is advantageously performed at atmospheric pressure, but higher pressures may also be envisioned. For example, pressures of between 5 and 10 bar may be suitable for use.

This step may advantageously be performed under an inert atmosphere, for example under nitrogen or under argon, nitrogen being preferred especially on account of its reduced cost.

The residence time and the temperature of the reaction medium in the mixing device must be appropriate for the chosen degree of conversion of hydrogen peroxide in said device.

The reaction mixture then passes from reactor (1) to reactor (2) by gravitational flow or by forced circulation, for example using a pump, usually a centrifugal pump.

In accordance with the process of the invention, a second step relative to the hydroxylation reaction is performed in a piston-flow reactor (2).

The reactor consists of a tube (9) through which circulate the reaction mixture which enters at (10) and the reaction products which leave at (11).

Usually, the reactor will have a length/diameter ratio of greater than 3. It may especially be a tubular reactor with a length/diameter ratio of between 4 and 30 and in particular between 5 and 10.

Advantageously, the tubular reactor is performed so as to have low bulk and makes it possible to increase the piston nature, for example when it is pushed back.

The material of the reactor is not particularly limited. It will be chosen so as to be inert under the reaction conditions. Generally, a stainless-steel reactor will be chosen.

Tubular reactors are generally arranged horizontally.

However, in order to adapt to the space constraints, it may also be envisioned to provide a reactor arranged vertically or inclined.

Advantageously, one or more perforated plates are arranged close to the reagent inlet so as to ensure good homogeneity of the fluids in this section of the reactor.

Advantageously, the tubular reactor is in column form. It is equipped with reagent inlet and reaction mixture outlet pipes.

The reagents are fed in via standard means, for instance a pump and more particularly a centrifugal pump or a volumetric pump.

In principle, it is preferable to work in the liquid phase only. The tubular reactor may be equipped with baffles.

The presence of baffles in the reactor creates turbulence which ensures homogeneity of the reaction mixture throughout the entire section of the reactor. The baffles thus make it possible to maintain the piston-flow nature, including the case of a Reynolds number of less than 5000.

The material of the baffles is unimportant, provided that it is chemically inert with respect to the reaction mixture under the reaction conditions. Generally, they are made of materials such as glass, metal, especially stainless steel, carbon, polymer or ceramic.

Various types of baffle may be envisioned. They may especially be:
  bulk baffles, which consist of small objects, for example in the form of rings, stools, balls or cylinders which are hollow, with which all or part of the reactor is filled
  structured baffles: pins, static mixers, chicanes.

Preferably, the baffles are arranged in the reactor close to the reagent inlet.

In the case of a reactor arranged vertically, the baffles are preferably arranged along the entire top of the reactor. It is then necessary to provide a suitable support, for example in the form of crossbeams, so as to hold the baffles in place.

Packing of static mixer type, composed of mixing elements comprising guide blades arranged at precise angles and positioned in a complex manner, is particularly preferred. This type of packing is sold, for example, by the company Sulzer under the names SMV and SMX.

For the description of these baffles, reference may be made to the article *Don't Be Baffled By Static Mixers* published in Chemical Engineering, May 2003.

From a practical point of view, a linear tube without baffles, folded back on itself and arranged horizontally or vertically when the Reynolds number is greater than 2000 and preferentially when it is greater than 5000, is chosen.

When the Reynolds number is less than 5000, a reactor without baffles may be used, by structuring it. For example, it is possible to fold the tubular reactor back on itself in the form of a helix or a succession of bends/straight lines; this structure may optionally be partially equipped with baffles. After each bend of the tube, a section of baffles of an equivalent length is inserted, for example from 3 to 6 times the diameter of the tube, over all or part of the straight length of the tube located between two successive bends.

The attached FIGS. 3 to 5 illustrate the types of apparatus that may be used as a piston-flow reactor.

FIG. 3 shows a tubular reactor formed from concentric tubes.

Thus, the reactor consists of a tube (14) through which circulate the reaction mixture which enters at (19) and the reaction products which leave at (20).

The heat exchange is provided by a heat-exchange fluid, circulating in a jacket (15), which enters at (17) and leaves at (18). The tube may contain packing sections after each bend (16).

FIG. 4 shows a reactor in column form (21) equipped with a jacket (22) or any equivalent means, in which circulates a heat-exchange fluid which enters at (23) and leaves at (24).

The column is equipped with baffles (25).

The reaction mixture is introduced at (26) and the products leave at (27).

It should be noted that the invention does not exclude the case in which a tubular reactor shown by FIG. 5 is of the vertical multi-tubular calendar heat exchanger type.

It comprises a reaction mixture introduction zone (28), a central zone (29) and a reagent outlet zone (30). The central zone comprises an array of parallel tubes (31); each tube comprising an inlet emerging in the inlet zone and an outlet emerging in the outlet zone.

The heat-exchange fluid entering at (32) and leaving at (33) circulates in the calendar (36) around the tubes.

The reaction mixture is introduced at (34) and the products leave at (35).

The tubes may or may not be equipped with baffles.

From the point of view of the process parameters, the temperature in said reactor (2) is higher than that of the mixing device. It is chosen to be higher than 70° C., preferably between 75° C. and 200° C. and more preferentially between 75° C. and 150° C.

In the process of the invention, the temperature of the hydroxylation reaction is maintained in the abovementioned temperature range by regulating the temperature using means conventionally used for temperature regulation and especially by circulating a heat-exchange fluid in the jacket.

In one embodiment, the reactor is an isothermal reactor.

FIG. 1 shows, purely for illustrative purposes, an isothermal reactor. The temperature in the reactor is provided by circulating a heat-exchange fluid through a jacket: the heat-exchange fluid is introduced at (12) and leaves at (13).

In another embodiment, the reactor is a reactor with temperature staging of the reaction medium, with various thermal zones.

The number of stages may range, for example, from 2 to 100 and preferably from 2 to 10.

The temperature in each stage is determined according to the desired degree of conversion of the hydrogen peroxide.

FIG. 2 shows, purely for illustrative purposes, a staged reactor. The different temperatures in each stage are ensured by circulating a heat-exchange fluid in a jacket at a different temperature: the heat-exchange fluid enters each stage at (12a) and (12b) and leaves at (13a) and (13b), respectively.

The temperature staging and the residence time of each zone are established to be appropriate for the reaction performance qualities (degree of conversion and yields).

This determination may be made in accordance with the publication by J. Villermaux (Génie de la réaction chimique; conception et fonctionnement des réacteurs [Chemical reaction engineering: design and functioning of reactors]; J. Villermaux; Tec & Doc Lavoisier; 1993) or that by O. Levenspiel (Chemical Reaction Engineering; $2^{nd}$ edition; Wiley Int.; 1972).

The staging of the temperature in the process according to the invention may also be performed in apparatus consisting of a series of tubular reactors maintained at different temperatures.

The reaction is advantageously performed at atmospheric pressure, but higher pressures may also be envisioned as previously.

This step may advantageously be performed under an inert atmosphere.

The invention will be explained in greater detail by means of examples that illustrate the invention without, however, limiting it.

In the examples, the following abbreviations have the meanings as follows:

The degree of conversion ($DC_{H2O2}$) of hydrogen peroxide corresponds to the ratio between the number of moles of hydrogen peroxide converted and the number of moles of hydrogen peroxide introduced.

The degree of conversion ($DC_{phenol}$) of phenol corresponds to the ratio between the number of moles of phenol converted and the number of moles of phenol introduced.

The diphenol reaction yield ($RY_{diphenols}$) corresponds to the ratio between the number of moles of diphenols formed (pyrocatechol+hydroquinone) and the number of moles of hydrogen peroxide introduced.

The pyrocatechol reaction yield ($RY_{pyrocatechol}$) corresponds to the ratio between the number of moles of pyrocatechol formed and the number of moles of hydrogen peroxide introduced.

The hydroquinone reaction yield ($RY_{hydroquinone}$) corresponds to the ratio between the number of moles of hydroquinone formed and the number of moles of hydrogen peroxide introduced.

The diphenol selectivity of ($TY_{diphenols}$) corresponds to the ratio between the number of moles of diphenols formed (pyrocatechol+hydroquinone) and the number of moles of hydrogen peroxide transformed.

The ratio PC/HQ is defined by the ratio between the number of moles of pyrocatechol and the number of moles of hydroquinone.

COMPARATIVE EXAMPLE 1

100 g/h (1.06 mol/h) of phenol containing pyrophosphoric acid (400 ppm by mass relative to the phenol), 2.94 g/h of hydrogen peroxide at 70% by weight (i.e. 0.0605 mol/h) and perchloric acid (250 mol ppm relative to the phenol) are fed, using pumps, into a 300 mL reactor in continuous mode, equipped with a jacket and a stirring system of the type with four inclined paddles, an ascending condenser, a nitrogen inlet and a temperature regulation device for maintaining the reaction medium at 90° C.

The outlet flow rate is adjusted to the reagent inlet flow rate so as to have a constant reaction volume adjusted to have a residence time of 70 minutes.

After a stabilization time (about 3 hours), the diphenols formed are assayed by high-performance liquid chromatography and the hydrogen peroxide is assayed by potentiometry.

The results are collated in table (I).

COMPARATIVE EXAMPLE 2

Phenol (containing pyrophosphoric acid in a proportion of 400 ppm by mass relative to the phenol), hydrogen peroxide and the catalyst are introduced in parallel and continuously into a cascade of 3 glass reactors with an overall volume of 300 mL.

Each jacketed reactor is equipped with a mechanical stirring system of the type with 4 inclined paddles, a temperature regulation system, an ascending condenser and a nitrogen inlet.

100 g/h (1.06 mol/h) of phenol, 2.94 g/h of hydrogen peroxide at 70% by weight (i.e. 0.0605 mol/h) and perchloric acid (250 mol ppm relative to the phenol) are introduced, with the aid of pumps.

The outlet flow rate is adjusted to the reagent inlet flow rate so as to have a constant reaction volume adjusted to have an overall residence time of 70 minutes.

The reactors are all at the same temperature: 90° C.

After a stabilization time (about 3 hours), the diphenols formed are assayed by high-performance liquid chromatography and the hydrogen peroxide is assayed by potentiometry.

The results obtained in the third reactor are given in table (I).

EXAMPLE 3

The following are introduced at 60° C. continuously, with the aid of pumps, into a jacketed reactor with a working volume of 30 mL, equipped with a stirring system of the type with 4 inclined paddles, an ascending condenser, a nitrogen inlet and a temperature regulation system:
  100 g/h (1.06 mol/h) of phenol containing pyrophosphoric acid in a proportion of 400 ppm by mass relative to the phenol,
  perchloric acid in a proportion of 250 mol ppm relative to the phenol,
  2.94 g/h of hydrogen peroxide at 70% by weight (i.e. 0.0605 mol/h of hydrogen peroxide).

The residence time in this reactor is 20 minutes.

The reaction medium of this reactor is introduced continuously, with the aid of a pump, into a jacketed tubular reactor packed with Sulzer SMX mixers, with an overall volume of 115 mL (length=255 mm, diameter=24 mm), and whose temperature is set at 90° C.

After a stabilization time (about 3 hours), the diphenols formed are assayed by high-performance liquid chromatography and the hydrogen peroxide is assayed by potentiometry.

The results obtained at the outlet of the tubular reactor are given in table (I).

TABLE (I)

| Example Reference | 1 comparative | 2 comparative | 3 |
|---|---|---|---|
| Type of reactor | 1 stirred reactor | 3 stirred reactors in cascade | 1 stirred reactor + 1 piston reactor |
| Catalyst | $HClO_4$ | $HClO_4$ | $HClO_4$ |
| $HClO_4$/PhOH (mol ppm) | 250 | 250 | 250 |
| Pyrophosphoric acid/PhOH (ppm by weight) | 400 | 400 | 400 |
| $H_2O_2$/PhOH (mol %) | 5.7 | 5.7 | 5.7 |
| Residence time (min) | 70 | 70 | 70 |
| DC PhOH | 4.0% | 4.6% | 5.1% |
| RY HQ | 25% | 30% | 33.5% |
| RY PC | 36% | 42% | 47.5% |
| RY (diphenols) | 61% | 72% | 81% |
| Production (diphenols) (g/h) | 4.0 | 4.8 | 5.4 |
| Ratio PC/HQ | 1.44 | 1.43 | 1.42 |
| DC $H_2O_2$ | 78% | 91% | 97% |
| TY (diphenols)/$H_2O_2$ | 78% | 79% | 83% |

This table demonstrates, by comparing Example 3 of the invention and the Comparative Examples 1 and 2, the advantage of performing the phenol hydroxylation reaction in the apparatus of the invention (stirred reactor+piston reactor) since, for a higher reaction progress than in Examples 1 and 2, for an equivalent residence time, the yield of diphenols is higher in Example 3.

COMPARATIVE EXAMPLE 4

Phenol (containing pyrophosphoric acid), hydrogen peroxide and the catalyst are introduced in parallel and continuously into a cascade of 3 glass reactors with an overall volume of 500 mL.

Each jacketed reactor is equipped with a mechanical stirring system of the type with 4 inclined paddles, a temperature regulation system, an ascending condenser and a nitrogen inlet.

165 g/h of phenol (containing pyrophosphoric acid in a proportion of 400 ppm by mass relative to the phenol), 4.8 g/h of hydrogen peroxide at 70% by weight and perchloric acid (250 mol ppm relative to the phenol) are fed in, with the aid of pumps.

The outlet flow rate is adjusted to the reagent inlet flow rate so as to have a constant reaction volume adjusted to have a residence time of 67 minutes.

The reactors are all at the same temperature: 110° C.

After a stabilization time (about 3 hours), the diphenols formed are assayed by high-performance liquid chromatography and the hydrogen peroxide is assayed by potentiometry.

The results obtained in the third reactor are given in table (II).

EXAMPLE 5

The following are introduced at 60° C. continuously, with the aid of pumps, into a jacketed reactor with a working volume of 30 mL, equipped with a stirring system of the type with 4 inclined paddles, an ascending condenser, a nitrogen inlet and a heating device:
  165 g/h of phenol containing pyrophosphoric acid in a proportion of 400 ppm by mass relative to the phenol,
  perchloric acid in a proportion of 250 mol ppm relative to the phenol,
  6.5 g/h of hydrogen peroxide at 70% by weight,
  The residence time in this reactor is 10 minutes.

The reaction medium of this reactor is introduced continuously, with the aid of a pump, into a jacketed tubular reactor packed with Sulzer SMX mixers, with an overall volume of 115 mL (length=255 mm, diameter=24 mm), and whose temperature is set at 110° C.

After a stabilization time (about 3 hours), the diphenols formed are assayed by high-performance liquid chromatography and the hydrogen peroxide is assayed by potentiometry.

The results obtained at the outlet of the tubular reactor are given in table (II).

TABLE (II)

| Example Reference | 4 comparative | 5 |
|---|---|---|
| Type of reactor | 3 stirred reactors in cascade | 1 stirred reactor + 1 piston reactor |
| Catalyst | $HClO_4$ | $HClO_4$ |
| $H_2O_2$/PhOH (mol %) | 5.60 | 7.65 |
| $HClO_4$/PhOH (mol ppm) | 250 | 250 |
| Pyrophosphoric acid/PhOH (ppm by weight) | 400 | 400 |
| T (° C.) | 110 | 110 |
| Residence time (min) | 67 | 42 |
| DC PhOH | 5.0% | 6.7% |
| RY HQ | 44% | 45% |
| RY PC | 30% | 30% |
| RY (diphenols) | 74% | 75% |
| Production (diphenols) (g/h) | 8.2 | 11.3 |
| PC/HQ | 1.53 | 1.52 |
| DC $H_2O_2$ | 100% | 100% |
| TY (diphenols)/$H_2O_2$ | 74% | 75% |

This table shows that the diphenol selectivities expressed relative to $H_2O_2$ are equivalent whether the process is performed either in a cascade of stirred reactors with a phenol conversion of 5%, or with a stirred reactor coupled to a tubular piston reactor with a phenol conversion of about 7%; the operating conditions being otherwise equal.

The apparatus used according to the invention (stirred reactor+tubular piston reactor) thus makes it possible to target higher degrees of conversion of phenol while at the same time conserving yields equivalent to those of a cascade of stirred reactors.

COMPARATIVE EXAMPLE 6

Phenol (containing pyrophosphoric acid), hydrogen peroxide and the catalyst are introduced in parallel and continuously into a cascade of 3 glass reactors with an overall volume of 500 mL.

Each jacketed reactor is equipped with a mechanical stirring system of the type with 4 inclined paddles, a temperature regulation system, an ascending condenser and a nitrogen inlet.

90 g/h of phenol (containing pyrophosphoric acid in a proportion of 400 ppm by mass relative to the phenol), 2.6 g/h of hydrogen peroxide at 70% by weight and perchloric acid (400 mol ppm relative to the phenol) are fed in, with the aid of pumps.

The outlet flow rate is adjusted to the reagent inlet flow rate so as to have a constant reaction volume adjusted to have a residence time of 115 minutes.

The reactors are all at the same temperature: 92° C.

After a stabilization time (about 5 hours), the diphenols formed are assayed by high-performance liquid chromatography and the hydrogen peroxide is assayed by potentiometry.

The results obtained in the third reactor are given in table (III).

EXAMPLE 7

The following are introduced at 60° C. continuously, with the aid of pumps, into a jacketed reactor with a working volume of 30 mL, equipped with a stirring system of the type with 4 inclined paddles, an ascending condenser, a nitrogen inlet and a heating device:
  234 g/h of phenol containing pyrophosphoric acid in a proportion of 400 ppm by mass relative to the phenol,
  perchloric acid in a proportion of 400 mol ppm relative to the phenol,
  9.2 g/h of hydrogen peroxide at 70% by weight,
  The residence time in this reactor is 8 minutes.

The reaction medium of this reactor is introduced continuously, with the aid of a pump, into a tubular reactor packed with Sulzer SMX mixers, with an overall volume of 330 mL (length=350 mm, diameter=35 mm), having 4 independent jacketed zones, of respective lengths 78 mm, 116 mm, 78 mm, 78 mm, and having successive temperatures of 75° C.-80° C.-92° C.-107° C.

After a stabilization time (about 5 hours), the diphenols formed are assayed by high-performance liquid chromatography and the hydrogen peroxide is assayed by potentiometry.

The results obtained at the outlet of the tubular reactor are given in table (III).

TABLE (III)

| Example Reference | 6 comparative | 7 |
|---|---|---|
| Type of reactor | 3 stirred reactors in cascade | 1 stirred reactor + 1 piston reactor |
| Catalyst | $HClO_4$ | $HClO_4$ |
| $H_2O_2$/PhOH (mol %) | 5.6 | 7.65 |

TABLE (III)-continued

| Example Reference | 6 comparative | 7 |
|---|---|---|
| $HClO_4$/PhOH (mol ppm) | 400 | 400 |
| Pyrophosphoric acid/PhOH (ppm by weight) | 400 | 400 |
| T (° C.) | 92 | 75-80-92-107 |
| Residence time (min) | 115 | 85 |
| DC PhOH | 4.8% | 6.7% |
| RY HQ | 31% | 33% |
| RY PC | 45% | 47% |
| RY (diphenols) | 76% | 80% |
| Production (diphenols) (g/h) | 4.4 | 16.4 |
| PC/HQ | 1.45 | 1.40 |
| DC $H_2O_2$ | 100% | 100% |
| TY (diphenols)/$H_2O_2$ | 76% | 80% |

This table shows that the diphenol selectivities expressed relative to $H_2O_2$ are better by performing the process in the apparatus of the invention comprising a stirred reactor and a tubular reactor functioning in piston mode and having temperature staging at a phenol conversion of about 7%, than in a cascade of stirred reactors with a phenol conversion of 5%, working at an isotherm of 92° C.

EXAMPLE 8

The following are introduced at 60° C. continuously into a jacketed 3 $m^3$ reactor, equipped with a stirring system of the type with 4 inclined paddles, an ascending condenser, a nitrogen inlet and a temperature regulator:
  18 240 kg/h of phenol,
  perchloric acid in a proportion of 400 mol ppm relative to the phenol,
  720 kg/h of hydrogen peroxide at 70% by weight, with the aid of pumps.
The residence time is 10 minutes.
The reaction medium of this reactor is taken up, with the aid of a pump, into a jacketed tubular reactor with an overall volume of 8.5 $m^3$ (length=11 m, diameter=1 m), packed with Sulzer SMX static mixers, and whose temperature is set at 110° C.
At the outlet of the tubular reactor, a sample is taken, on which are assayed the diphenols formed by high-performance liquid chromatography, and the hydrogen peroxide by potentiometry.
The results obtained at the outlet of the tubular reactor are given in table (IV).

TABLE (IV)

| Example Reference | 8 |
|---|---|
| Type of reactor | 1 stirred reactor + 1 piston reactor |
| Catalyst | $HClO_4$ |
| $H_2O_2$/PhOH (mol %) | 7.65 |
| $HClO_4$/PhOH (mol ppm) | 400 |
| Pyrophosphoric acid/PhOH (ppm by weight) | 400 |
| T (° C.) | 110 |
| Residence time (min) | 28 |
| DC PhOH | 6.7% |
| RY HQ | 30% |
| RY PC | 46% |
| RY (diphenols) | 76% |
| Production (diphenols) (kg/h) | 1250 |

TABLE (IV)-continued

| Example Reference | 8 |
|---|---|
| PC/HQ | 1.52 |
| DC $H_2O_2$ | 99% |
| TY (diphenols)/$H_2O_2$ | 77% |

EXAMPLE 9

In this example, a reactor is used comprising a T-shaped connection, serving as mixer (T mixer), connected to a 316L stainless-steel jacketed piston-flow reactor. Such a piston-flow reactor is described in patent application WO 2011/117 540.

A flap valve tared at 5 bar absolute at the reactor outlet makes it possible to maintain the reaction medium always in the liquid phase. The T mixer is a standard connection produced by Swagelok in 1/16 inch, and is maintained at 50° C. (electrical resistance). The piston-flow reactor is of the tube-calendar type, with an internal volume of 7 ml and an inside diameter of 1/8 inch.

The tubular reactors that were used are tubes with inside diameters of 1/8 inch and their length was adjusted as a function of the residence time. This tube was wound so as to obtain practically but-jointed turns and a compact coil. This coil was enclosed in a chamber in which circulates a heat-exchange fluid for heating/cooling the tubes. The circulation of the heat-exchange fluid and the control of its temperature were ensured by means of a thermostatically regulated circulation bath. The tubular reactor is of the piston-flow type since it is equivalent to more than 60 perfectly stirred cascade reactors, for a flow rate of between 0.2 and 10 $g \cdot min^{-1}$. This reactor is heated via a flow of 47V50 silicone oil so as to maintain a temperature of 165° C. in the reaction medium.

Phenol feeds the T mixer at a flow rate of 4.8 $g \cdot min^{-1}$ via a syringe pusher heated to 50° C., so as to keep the phenol liquid. This same stream also contains the homogeneous catalyst (perchloric acid $HClO_4$) in a proportion of 230 mol ppm, and also phosphoric acid at a concentration of 200 ppm by mass. An aqueous 70 w/w % hydrogen peroxide solution feeds the other bar of the T mixer (in the opposite direction or head to tail) at a flow rate of 12 $g \cdot h^{-1}$.

Under such conditions, 20 minutes after reaching the permanent regime (detected by two samples taken 5 minutes apart), the residence time in the reactor is 1.2 minutes and the following performance is obtained:
  Conversion of $H_2O_2$=97 mol %;
  selectivity toward hydroquinone and catechol relative to $H_2O_2$=74 mol %;
  selectivity toward hydroquinone and catechol relative to phenol=84 mol %;
  catechol/hydroquinone mole ratio=1.68;
w/w % meaning % by weight relative to the total weight of the sample.

EXAMPLE 10

A C276 Hastelloy micromixer is used in this example, connected to a 316L stainless-steel jacketed piston-flow reactor. A flap valve tared at 5 bar absolute at the reactor outlet makes it possible to maintain the reaction medium always in the liquid phase. The micromixer was manufactured by the German company IMM under the reference SuperFocus Interdigital Micromixer SFIMM-V2, and is insulated and maintained at 50° C. (electrical resistance). The piston-flow reactor is identical to that of example 9. This reactor is heated via a flow of 47V50 silicone oil so as to maintain a temperature of 165° C. in the reaction medium. Phenol feeds the micromixer at a flow rate of 1.2 g·min$^{-1}$ via a syringe pusher heated to 50° C., so as to keep the phenol liquid. This same stream also contains the homogeneous catalyst (perchloric acid HClO$_4$) in a proportion of 230 mol ppm, and also phosphoric acid at a concentration of 200 ppm by mass. An aqueous 70 w/w % hydrogen peroxide solution separately feeds the micromixer at a flow rate of 3 g·h$^{-1}$.

Under such conditions, 20 minutes after reaching the permanent regime (detected by two samples taken 5 minutes apart), the residence time in the reactor is about 5 minutes and the following performance is obtained:
Conversion of H$_2$O$_2$=100 mol %;
selectivity toward hydroquinone and catechol relative to H$_2$O$_2$=74 mol %;
selectivity toward hydroquinone and catechol relative to phenol=83 mol %;
catechol/hydroquinone mole ratio=1.68.

EXAMPLE 11

This example concerns a plate-type heat exchange reactor. The device may comprise a T-shaped connection (T mixer), connected to the 316L stainless-steel plate-type heat exchange reactor. The circulation of the heat-exchange fluid and the control of its temperature may be ensured by means of a thermostatically regulated circulation bath. A flap valve tared at 5 bar absolute at the reactor outlet makes it possible to maintain the reaction medium always in the liquid phase. The T mixer is a standard connection produced by Swagelok in ⅛ inch.

A heat exchanger reactor containing 3 plates etched with a channel about 2 mm in diameter, which gives it an internal volume of 37 ml and an exchange surface of 0.074 m$^2$, may be used. The specific heat exchange coefficient is then about 8000 kW·m$^{-3}$·K$^{-1}$. Each of the three plates is arranged between 2 "utility" plates in which circulates a heat-exchange fluid (47V50 silicone oil) so as to maintain a temperature of 145° C. in the reaction medium. Phenol can feed the T mixer at a flow rate of 0.65 kg·h$^{-1}$ via a pump with a head heated to and maintained at 50° C., so as to keep the phenol liquid. This same stream may also contain the homogeneous catalyst (perchloric acid HClO$_4$) in a proportion of 230 mol ppm, and also phosphoric acid at a concentration of 200 ppm by mass. An aqueous 70 w/w % hydrogen peroxide solution can feed the other bar of the T mixer counter-currentwise at a flow rate of 26 g·h$^{-1}$, via a syringe pusher under pressure.

Under such conditions, 20 minutes after reaching the permanent regime, the residence time in the plate-type heat exchange reactor will be 3.3 minutes, the temperature profile will be remarkably flat and the following performance will be obtained:
Conversion of H$_2$O$_2$=98 mol %;
selectivity toward hydroquinone and catechol relative to H$_2$O$_2$=76 mol %;
selectivity toward hydroquinone and catechol relative to phenol=87 mol %;
catechol/hydroquinone mole ratio=1.61.

EXAMPLE 12

The same device as for example 11 may be used, with a phenol flow rate of 3,6 kg·h$^{-1}$, and with a flow rate of aqueous 70 w/w % hydrogen peroxide solution of 144 g·h$^{-1}$, injected separately into the T mixer via piston pumps under pressure.

Under such conditions, 20 minutes after reaching the permanent regime, the residence time in the plate-type heat exchange reactor will be 0.6 minute, the temperature profile will be remarkably flat and the following performance will be obtained:
Conversion of H$_2$O$_2$=69 mol %;
selectivity toward hydroquinone and catechol relative to H$_2$O$_2$=83 mol %;
selectivity toward hydroquinone and catechol relative to phenol=93 mol %;
catechol/hydroquinone mole ratio=1.62.

The invention claimed is:

1. A process for hydroxylation of a phenol or of a phenol ether, the process comprising:
mixing a phenol or phenol ether with a hydrogen peroxide solution to form a reaction mixture in a mixing device under conditions such that the degree of conversion of hydrogen peroxide is less than 25% by mol;
introducing said reaction mixture into a piston-flow reactor in which takes place a hydroxylation reaction of said phenol or phenol ether with hydrogen peroxide leading to the formation of a hydroxylated product; and
introducing a strong protic acid catalyst having a pKa in water of less than −0.1 into the mixing device and/or into the piston-flow reactor.

2. The process as claimed in claim 1, wherein the temperature in the mixing device is less than or equal to 700.

3. The process as claimed in claim 1, wherein the mixing device is a mechanically stirred reactor; a turbine reactor with straight or inclined paddles or with a marine impeller or a mobile "hydrofoil"; a reactor, mechanically stirred or not, with a loop for circulation of a fraction or all of the contents of said reactor, with the aid of a pump on an external loop; a dynamic mixer; a mixer with tangential jets, with impact jets or ejectors; a static mixer; or a static mixer with a bulk bed of beads or particles, metallic or ceramic foams.

4. The process as claimed in claim 1, wherein an exchange surface for heat transfer is increased by means of coils or plates present inside the piston-flow reactor or via a heat-exchange fluid circulating in a jacket.

5. The process as claimed in claim 1, wherein said phenol or phenol ether, said hydrogen peroxide solution, optionally a complexing agent and/or a solvent are introduced into the mixing device; and wherein the strong protic acid catalyst is introduced into the mixing device and/or into the piston-flow reactor.

6. The process as claimed in claim 1, wherein the temperature in the piston-flow reactor is greater than 70° C.

7. The process as claimed in claim 1, wherein the piston-flow reactor is a tubular reactor which has a length/diameter ratio of greater than 3.

8. The process as claimed in claim 1, wherein the piston-flow reactor is a tubular reactor arranged horizontally, vertically or inclined.

9. The process as claimed in claim 1, wherein the piston-flow reactor comprises baffles when the flow in the piston-flow reactor has a Reynolds number of less than 5000.

10. The process as claimed in claim 1, wherein the piston-flow reactor does not comprise baffles when the flow in the piston-flow reactor has a Reynolds number of greater than or equal to 5000.

11. The process as claimed in claim 1, wherein the piston-flow reactor is structured when the Reynolds number is less than 5000; said structured reactor optionally being partially equipped with baffles.

12. The process as claimed in claim 9, wherein the reactor is totally or partially filled with bulk baffles selected from the group consisting of rings, stools, balls, and cylinders which are hollow, or wherein the reactor comprises structured baffles selected from the group consisting of pins, static mixers, and chicanes.

13. The process as claimed in claim 1, wherein the piston-flow reactor is a tubular reactor formed from concentric tubes, a reactor in column form, or a tubular reactor comprising tubes assembled in an array.

14. The process as claimed in claim 1, wherein the reactor is an isothermal reactor or a reactor with temperature staging of the reaction mixture comprising from 2 to 100 stages.

15. The process as claimed in claim 14, wherein the reaction temperature is staged using a staged reactor with different temperatures in each stage ensured by circulating a heat-exchange fluid in a jacket at a different temperature or by using an apparatus consisting of a series of tubular reactors maintained at different temperatures.

16. The process as claimed in claim 1, wherein the phenol or phenol ether corresponds to general formula (I):

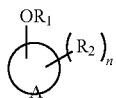

(I)

wherein in said formula (I):
A symbolizes a benzene or naphthalene ring,
$R_1$ represents a hydrogen atom or an alkyl, cycloalkyl, aryl or aralkyl group,
$R_2$ represents a hydrogen atom or one or more identical or different substituents,
n, number of substituents per aromatic ring, is a number less than or equal to 4.

17. The process as claimed in claim 16, wherein the phenol or phenol ether corresponds to the general formula (Ia):

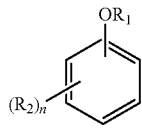

(Ia)

wherein in said formula (Ia):
n is a number from 0 to 4,
$R_1$ represents a hydrogen atom or an alkyl, cycloalkyl, aryl or aralkyl group,
$R_2$, being identical or different, represent an alkyl group, an alkoxy group, a hydroxyl group, a halogen atom, a haloalkyl group, or a perhaloalkyl group.

18. The process as claimed in claim 17, wherein the phenol or phenol ether is phenol, o-cresol, m-cresol, p-cresol, anisole, phenetole, 2-methoxyphenol (guaiacol), or 2-ethoxyphenol (guetol).

19. The process as claimed in claim 1, wherein the strong protic acid catalyst is a mixture of protic acids.

20. The process as claimed in claim 1, wherein the strong protic acid catalyst is selected from the group consisting of sulfuric acid, perchloric acid, methanesulfonic acid, trifluoromethanesulfonic acid, toluenesulfonic acid, phenolsulfonic acid, bis-trifluoromethanesulfonimide, a mixture of perchloric acid and sulfuric acid; a mixture of perchloric acid and 4-hydroxybenzenesulfonic acid; a mixture of trifluoromethanesulfonic acid and 4-hydroxybenzenesulfonic acid; and a mixture of bis-trifluoromethanesulfonimide and 4-hydroxybenzenesulfonic acid.

21. The process as claimed in claim 1, wherein a ketone compound is added, which corresponds to general formula (II):

(II)

wherein in said formula (II):
$R_a$ and $R_b$, being identical or different, represent hydrocarbon-based groups containing from 1 to 30 carbon atoms or together form a divalent group, optionally substituted with one or more halogen atoms or functional groups that are stable under the reaction conditions,
X represents a valency bond, a —CO— group, a —CHOH group or a group —(R)$_n$—: R representing an alkylene group and n is an integer chosen between 1 and 16.

22. The process as claimed in claim 21, wherein the ketone compound corresponds to the general formula (IIa) below:

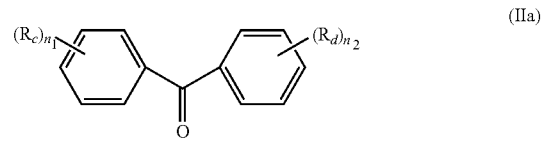

(IIa)

wherein in said formula (IIa):
$R_c$ and $R_d$, being identical or different, represent a hydrogen atom or a substituent,
$n_1$ and $n_2$, being identical or different, represent a number equal to 0, 1, 2 or 3,
optionally, the two carbon atoms located α to the two carbon atoms bearing the —CO group are linked together via a valency bond or via a —CH$_2$— group, thus forming a ketone ring, which is saturated or unsaturated.

23. The process as claimed in claim 1, wherein an aqueous hydrogen peroxide solution having an H$_2$O$_2$ concentration of at least 20% by weight is used.

24. The process as claimed in claim 1, wherein said reaction is performed in the presence of an agent for complexing transition metal ions, which is stable under the reaction conditions.

* * * * *